(12) United States Patent
Boehm et al.

(10) Patent No.: US 9,469,464 B2
(45) Date of Patent: Oct. 18, 2016

(54) MICROFLUIDIC DISPENSER, CARTRIDGE AND ANALYSIS SYSTEM FOR ANALYZING A BIOLOGICAL SAMPLE

(71) Applicant: Roche Diagnostics Operations, Inc., Indianapolis, IN (US)

(72) Inventors: Christoph Boehm, Viernheim (DE); Timo Klein, Altdorf (DE); Peter Koltay, Freiburg (DE); Nadine Losleben, Mannheim (DE); Juergen Spinke, Lorsch (DE); Chris Steinert, Freiburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/530,861

(22) Filed: Nov. 3, 2014

(65) Prior Publication Data
US 2015/0048119 A1 Feb. 19, 2015

Related U.S. Application Data

(63) Continuation of application No. PCT/EP2013/059478, filed on May 7, 2013.

(30) Foreign Application Priority Data

May 8, 2012 (EP) .................................... 12167109

(51) Int. Cl.
*B65D 83/14* (2006.01)
*B01L 3/02* (2006.01)
(Continued)

(52) U.S. Cl.
CPC ............ *B65D 83/14* (2013.01); *B01L 3/0265* (2013.01); *B01L 3/502738* (2013.01);
(Continued)

(58) Field of Classification Search
CPC .......... B01L 3/0265; B01L 3/502738; B01L 3/505; B01L 5/523; B01L 3/527; B01L 2300/123; B01L 2400/0611; G01N 35/1016; B65D 83/14

USPC ......................................................... 222/207
See application file for complete search history.

(56) References Cited

U.S. PATENT DOCUMENTS 4,130,224 A * 12/1978 Norman ................ G01F 11/088
222/181.2
4,515,294 A * 5/1985 Udall ................... B65D 77/065
222/105
(Continued)

FOREIGN PATENT DOCUMENTS

EP 1959257 A2 8/2008
EP 2374541 A1 10/2011
(Continued)

OTHER PUBLICATIONS

International Search Report issued Jul. 17, 2013 in Application No. PCT/EP2013/059478, 4 pages.
(Continued)

*Primary Examiner* — Nichols J Weiss
(74) *Attorney, Agent, or Firm* — Roche Diagnostics Operations, Inc.

(57) ABSTRACT

A dispenser for dispensing a fluid is presented. The dispenser comprises a compressible elastomeric fluid conduit having a first end and a second end for flowing the fluid from the first end to the second end, a first check valve and a second check valve distanced in the conduit for forming a fluid chamber, and an actor for compressing the fluid chamber for dispensing a portion of the fluid. At least the second check valve is a duckbill valve. The second check valve is located at the second end of the conduit. The second check valve has sealing lips that extend beyond the second end of the conduit.

9 Claims, 11 Drawing Sheets

(51) Int. Cl.
   *B01L 3/00*   (2006.01)
   *G01N 35/10*  (2006.01)

(52) U.S. Cl.
   CPC .......... *G01N 35/1016* (2013.01); *B01L 3/505* (2013.01); *B01L 3/523* (2013.01); *B01L 3/527* (2013.01); *B01L 2300/123* (2013.01); *B01L 2400/0611* (2013.01)

(56) References Cited

U.S. PATENT DOCUMENTS

| | | | | |
|---|---|---|---|---|
| 4,776,495 | A | * | 10/1988 | Vignot ................. A47K 5/1209 222/206 |
| 5,082,150 | A | * | 1/1992 | Steiner ................. B67D 1/0079 222/189.09 |
| 5,456,284 | A | | 10/1995 | Ryan et al. |
| 5,947,167 | A | | 9/1999 | Bogen et al. |
| 6,092,695 | A | * | 7/2000 | Loeffler ................. B01L 3/0296 137/859 |
| 7,346,141 | B2 | * | 3/2008 | Payne .................... G21C 3/334 376/362 |
| 7,501,283 | B2 | * | 3/2009 | Hersch .................. B01L 3/0265 222/144 |
| 8,678,244 | B2 | * | 3/2014 | Yang .................... A47K 5/1202 222/321.9 |
| 2012/0248147 | A1 | * | 10/2012 | Krom .................... B01F 9/0021 222/135 |

FOREIGN PATENT DOCUMENTS

| | | |
|---|---|---|
| WO | 2005/016534 A1 | 2/2005 |
| WO | 2006/048643 A1 | 5/2006 |
| WO | 2007/122387 A3 | 11/2007 |

OTHER PUBLICATIONS

Streule, W. et al., "PipeJet: A Simpmle Disposable Dispenser for the Nano- and Microliter Range," JALA, Oct. 2004, pp. 300-306, vol. 9.

* cited by examiner

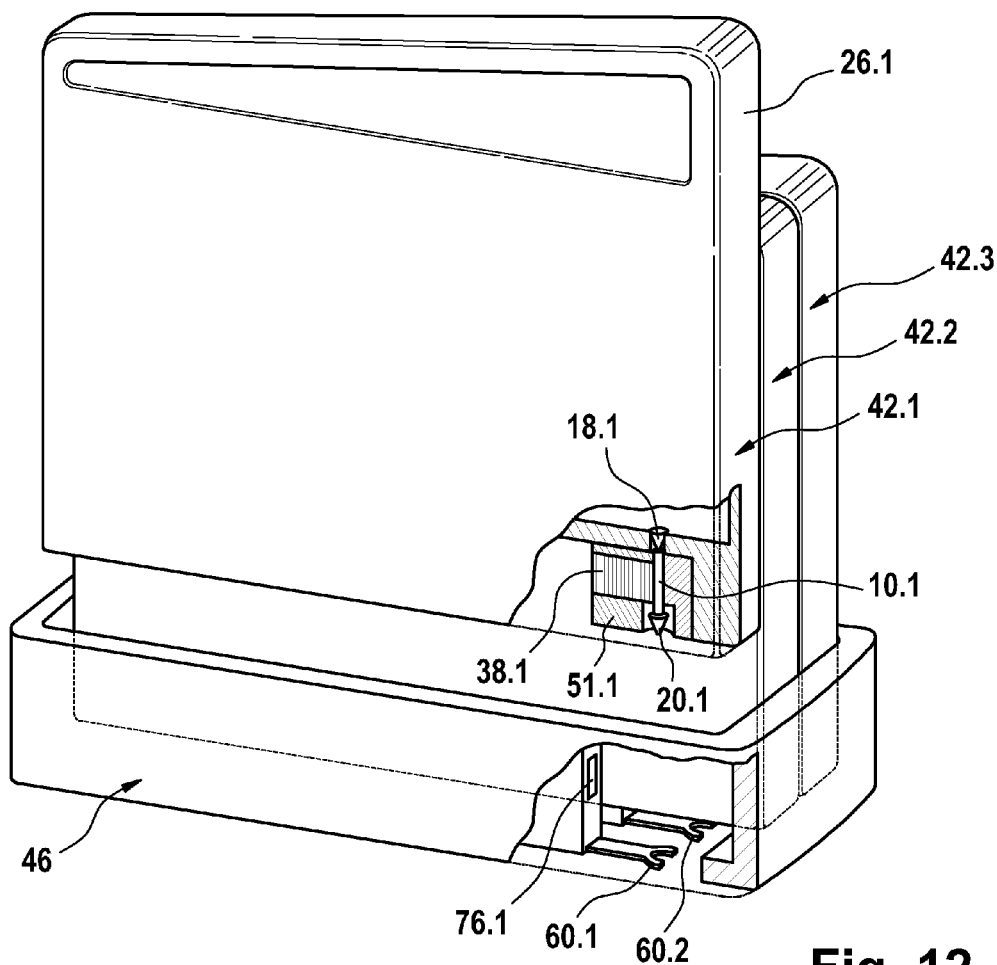
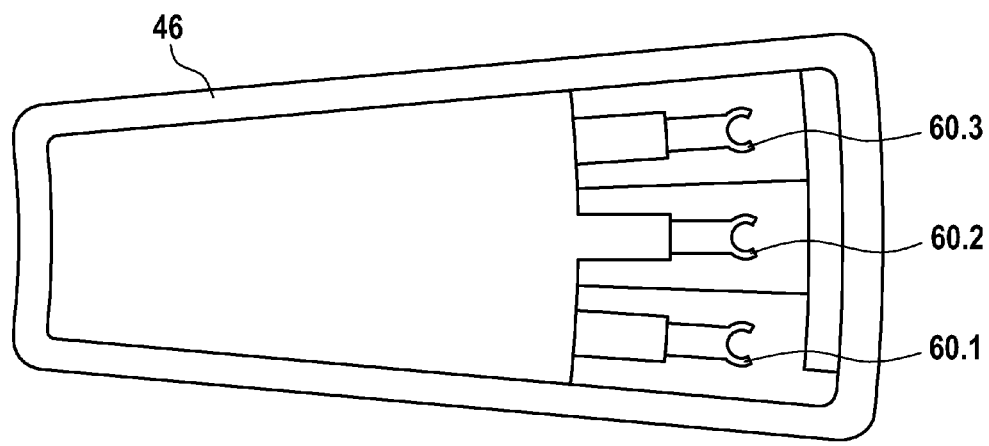

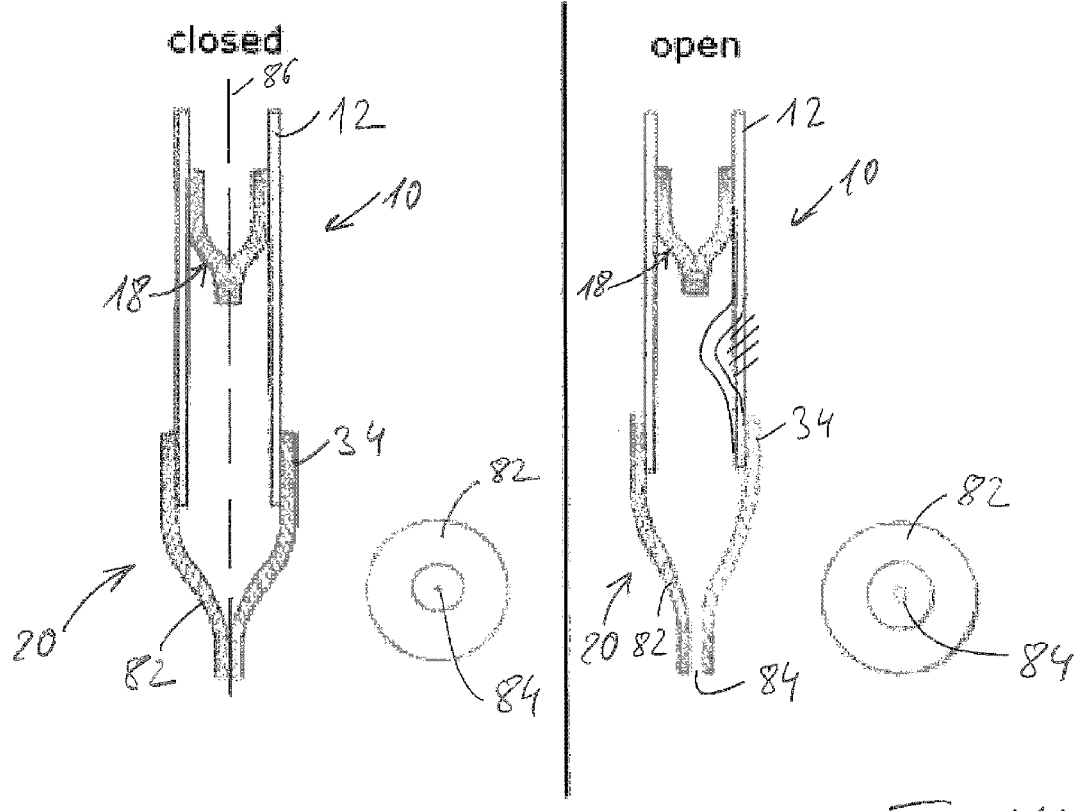

US 9,469,464 B2

MICROFLUIDIC DISPENSER, CARTRIDGE AND ANALYSIS SYSTEM FOR ANALYZING A BIOLOGICAL SAMPLE

CROSS-REFERENCE TO RELATED APPLICATIONS

This application is a continuation of PCT/EP2013/059478, filed May 7, 2013, which is based on and claims priority to EP 12167109.3, filed May 8, 2012, which is hereby incorporated by reference.

BACKGROUND

The present disclosure generally relates to microfluidic dispensers, cartridges and analysis systems for analyzing biological samples.

It is an object of the present disclosure to provide an improved microfluidic dispenser, a cartridge and an analysis system over those dispensers, cartridges and analysis systems known in the art.

SUMMARY

According to the present disclosure, a microfluidic dispenser, a cartridge and an analysis system for dispensing a fluid are presented. The dispenser comprises a compressible elastomeric fluid conduit having a first end and a second end for flowing the fluid from the first end to the second end, a first check valve and a second check valve distanced in the conduit for forming a fluid chamber, and an actor for compressing the fluid chamber for dispensing a portion of the fluid. At least the second check valve is a duckbill valve or a rotationally symmetrical valve having a circular fluid outlet. The second check valve is located at the second end of the conduit. The second check valve forms a sealing surface that extends beyond the second end of the conduit. The sealing surface of the second check valve forms part of the outer surface of the dispenser such that the fluid is dispensed directly from the second check valve.

Accordingly, it is a feature of the embodiments of the present disclosure to provide an improved microfluidic dispenser, a cartridge and an analysis system. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 11 illustrates a perspective view of an embodiment of a cartridge according to an embodiment of the present disclosure.

FIG. 12 illustrates a top view of the docking station of the embodiment of FIG. 11 according to an embodiment of the present disclosure.

FIG. 16a illustrates a longitudinal cross-sectional view of a further embodiment of a microfluidic dispenser in its normally-closed state according to an embodiment of the present disclosure.

FIG. 16b illustrates a bottom view of the symmetrical valve in its normally-closed state according to an embodiment of the present disclosure.

FIG. 17a illustrates a longitudinal cross-sectional view of the further embodiment of FIG. 16 in the open state according to an embodiment of the present disclosure.

FIG. 17b illustrates a bottom view of the symmetrical valve in its open state according to an embodiment of the present disclosure.

DETAILED DESCRIPTION

Figure 1:
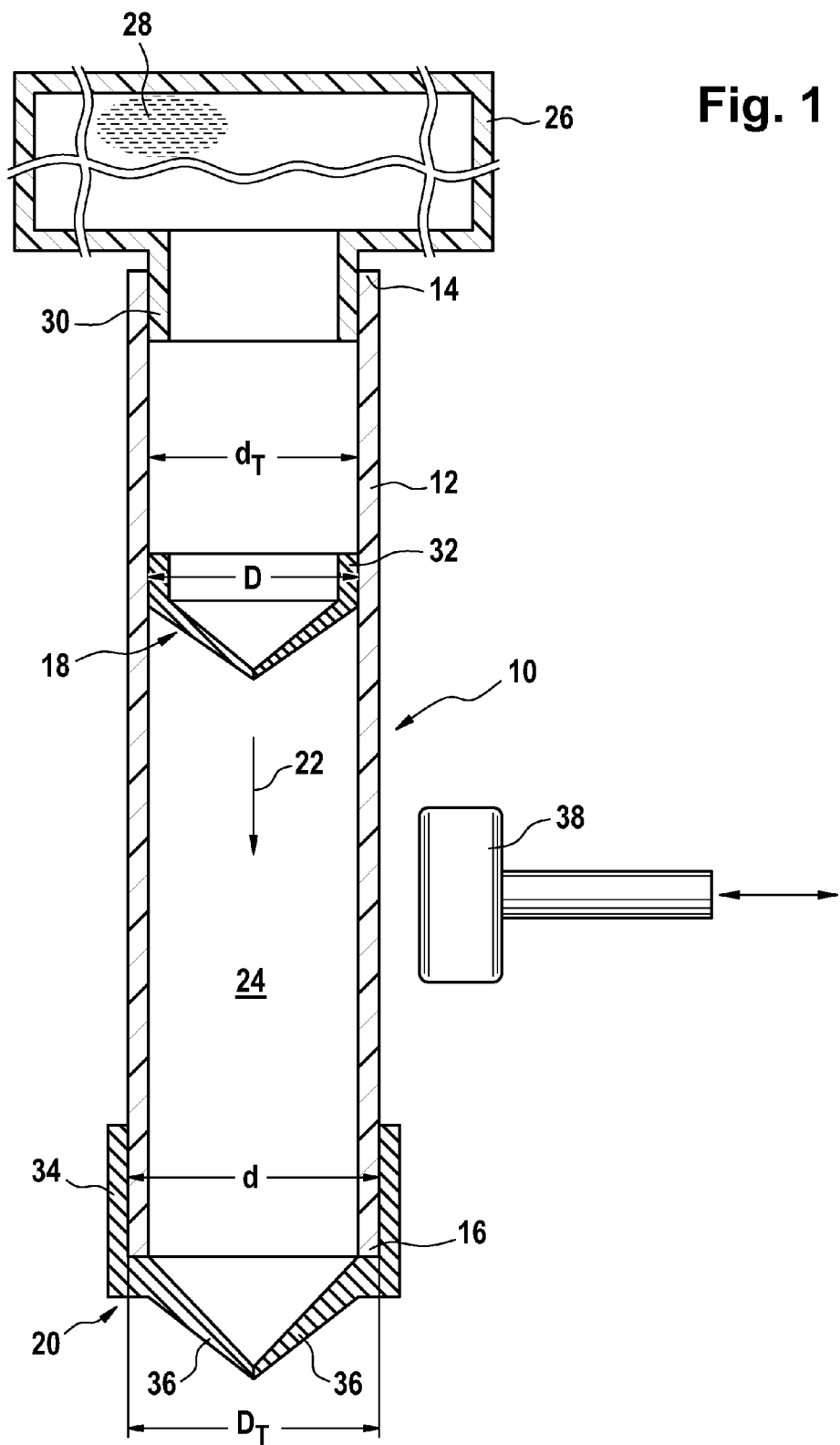
FIG. 1 illustrates a longitudinal cross-sectional view of a microfluidic dispenser according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

In accordance with some embodiments, a microfluidic dispenser is provided for dispensing a fluid, such as, for example, a reagent. The microfluidic dispenser can comprise a compressible elastomeric fluid conduit, such as, for example, an elastomeric tube. First and second check valves can be mounted in the conduit. The first and second check valves can be distanced in the direction of fluid flow within the conduit for forming a fluid chamber in the conduit.

In accordance with some embodiments, the microfluidic dispenser can have an actor for compressing the fluid chamber formed in the conduit for dispensing a portion of the fluid. Alternatively, the actor may not be part of the microfluidic dispenser but of an external device, such as an analyzer, that may also comprise a drive for driving the actor.

In accordance with an embodiment, at least the second check valve can be a duckbill valve that can be located at the end of the conduit from where the fluid can be dispensed. The second check valve can have sealing lips, such as, for example, elastomeric sealing lips, that can extend beyond the second end of the conduit.

A "duckbill valve" as understood herein can encompass a valve, manufactured, for example, from rubber or synthetic elastomer, and shaped like the beak of a duck. A duckbill valve may have an outlet slit formed by adjacent sealing lips that may have the form of a straight line. Other forms can also be possible for the outlet such as a cross slot or a T-shape.

The term "microfluidic" as understood herein can encompass fluid volumes in the nanoliter or microliter range, such as between about 1 nanoliter and about 10 microliter.

In accordance with some embodiments, the second check valve can be a rotationally symmetrical valve that can have a circular fluid outlet. In one embodiment, the second check valve can have a symmetrical valve body that can be symmetrical around a longitudinal axis of symmetry that it can extend along the fluid conduit. The circular fluid outlet of the second check valve can be centered on the axis of symmetry. The second check valve can be made of an elastic material that can have an elastic pre-tension to keep the circular fluid outlet normally-closed.

The rotational symmetry of the second check valve and, in particular, its circular fluid outlet can have the advantage that the fluid can be dispensed from the second check valve with a quasi-laminar fluid flow profile that can prevent the creation of so called 'satellites' when the fluid is dispensed such that the precision with which the fluid is dispensed can be further increased and the adhesion of fluid residuals on the dispenser can be reduced.

In accordance with some embodiments, the elastic material of the second check valve may comprise silicone, a thermoplastic elastomer (TPE) and/or vulcanized rubber. The second check valve having the elastic pre-tension can be produced by injection molding, injection-compression or hot-stamping.

The term 'normally-closed' as understand herein can relate to a valve that can be operated by an actor, such as by exercising a mechanical force onto the compressible elastomeric fluid conduit. The valve can be in its closed state if the actor is not energized or if the actor or drive of the actor fails. In other words, unless an opening force is exercised from the actor onto the valve, such as by compressing the elastomeric fluid conduit, the valve can remain in its closed position.

The term "actor" as understood herein can relate to a mechanical contact element that can be driven to mechanically act upon another element, for example, the elastomeric fluid conduit, by exercising a mechanical force.

Some embodiments can be particularly advantageous as the second check valve can have an additional function: it can keep the valve normally-closed and can provide evaporation protection to prevent evaporation of the fluid contained in the compressible elastomeric fluid conduit.

Some embodiments can be particularly advantageous as the entirety of the fluid that is dispensed from the fluid chamber through the second check valve can be dispensed into a receptacle, such as a test tube. Essentially nothing of the dispensed fluid volume can remain on the outside of the microfluidic dispenser. This can have the advantage that no decay products of a portion of the dispensed fluid volume that may otherwise adhere to the outside of the microfluidic dispenser may be present. This can prevent the dispensed fluid from being contaminated by such decay products which may result from the contact with the dispensed fluid with the ambient air.

Another advantage can be that the concentration of a reagent which is dispensed may not be changed by remaining fluid volumes of former dispensing steps. Due to evaporation of the solvent of the reagent volumes adhering on the outside of the microfluidic dispenser, the reagent concentration within this adhering and remaining reagent volume from a former dispensing step can increase during time and may influence the overall reagent concentration of the subsequent dispensing steps. This way a potential error can be eliminated which can enable to further increase the precision with which a desired quantity of a reagent with a defined and reproducible concentration can be dispensed.

Another advantage can be that the purity of the fluid may not be negatively affected by the dispensing process such that the volume of the dispensed fluid may be decreased, especially if the fluid is a reagent.

This can also be due to the fact that the microfluidic dispenser can have no dead volume into which a portion of the dispensed fluid volume is retained in contact with the ambient air. Furthermore, this can be because of the surprising effect of the second check valve, i.e. the duckbill valve or the rotationally symmetrical valve, acting as a nozzle. This can result in a quasi-laminar fluid flow during the fluid dispensing process and a defined cut-off of the fluid flow when the dispensing terminates after the desired fluid volume has been dispensed from the fluid chamber.

The precise and defined cut-off of the fluid dispensing flow can be due to the duckbill valve which may have an outlet slit formed by the adjacent sealing lips that preferably can have the form of a straight line. This way a well-defined edge can be formed by the outlet slit for cutting off the fluid flow at the end of the dispensing process.

This effect can also be accomplished using the rotationally symmetrical valve. The rotationally symmetrical valve can have the further advantage that the creation of turbulences can be prevented due to the symmetrical design so that a perfectly laminar fluid flow may result.

The resultant quasi deterministic dispensing process for dispensing the fluid can have the advantage that essentially nothing of the dispensed fluid volume can remain on the outside of the sealing lips of the second check valve, flange of the second check valve or other parts of the microfluidic dispenser. In addition, this can have the advantage of increased precision as the entirety of the dispensed fluid volume does in fact reach the receptacle.

Some embodiments can be particularly advantageous as any risk of cross-contamination, especially sample-to-sample cross-contamination (also known as sample carry-over), can be avoided as the dispensing of fluid can be performed contactlessly, i.e. without establishing a contact between the outlet of the dispenser and the vessel into which the fluid is dispensed.

In accordance with one embodiment, the second check valve can be mounted on the second end of the conduit by a slip-fit. This can have the advantage of enabling an efficient assembly while preventing the creation of a dead volume for the dispensed fluid.

In accordance with one embodiment, the second check valve can have an inner diameter ($d_T$) below about 0.8 mm; in another embodiment, below about 0.7 mm; and in yet another embodiment, below 0.6 mm.

In accordance with one embodiment, the first check valve can be mounted within the conduit forming a slip-fit and/or by forming a slip-fit with a connecting piece of a fluid reservoir to which the dispenser can be attached.

A 'slip-fit' as understood herein can be created by the part that is mounted on another part having a dimension that may not precisely fit or match the other part on which it is mounted resulting in a deformation which can be also referred to as 'press-fit'.

In accordance with some embodiments, the microfluidic dispenser including the first and second check valves can be a mold part that can be produced by multi-component injection molding.

A cartridge for dispensing fluid is provided. The cartridge can have a reservoir for the fluid. The microfluidic dispenser can be attached to a connecting piece of the reservoir.

In accordance with one embodiment, the cartridge can have a wall portion that can serve as a counter-bearing for the actor. The fluid chamber of the dispenser can extend along the wall portion. When the actor presses the fluid chamber against the wall portion, the fluid chamber can be compressed such that fluid can be dispensed. This design can have the advantage of integrating the counter-bearing into the cartridge.

In accordance with one embodiment, the cartridge can have a holder for holding the actor in proximity to the fluid chamber and for guiding the actor towards the chamber when the actor is urged against the chamber by a drive. This can have the advantage of integrating the actor into the cartridge.

In accordance with one embodiment, the cartridge can receive an actor from an external device, such as from an analyzer. The external device can have a drive for urging the actor against the chamber when the cartridge is in an operating position. This can have the advantage of reducing the number of components that may be integrated into the cartridge and thus the cost of production of the cartridge.

In accordance with some embodiments, the actor can have a drive coupler for releasably coupling the actor to the drive. For example, the actor may be a push rod. One end of the push rod can compress the fluid chamber whereas the other end of the actor can carry a ferromagnetic element for coupling the actor to the drive when the cartridge is inserted into an analysis system.

In accordance with one embodiment, a chuck, such as, for example, a jawed chuck, a vacuum chuck or a collet, can be used for releasably coupling the actor to the drive.

An analysis system for analyzing a biological sample, such as by an immunoassay is presented. For execution of such an analysis, one or more reagents may be required that need to be mixed with the biological sample in order to perform a reaction that can be sensed by the analysis system.

The analysis system can have a cartridge holder for holding a plurality of the cartridges that can be filled with the various reagents that may be required for the performance of the analysis. The analysis system can further comprise a receptacle holder for holding a receptacle for receiving the biological sample and one or more of the reagents, such as a sample tube holder or sample tube gripper.

The analysis system can further comprise a robotic component for relative movement of the receptacle holder and the cartridge holder for moving one of the cartridges that can be filling with a required reagent over the receptacle for ejecting a portion of the fluid into the receptacle in order to bring the reagent into contact with the biological sample. In other words, either the receptacle holder can be moved or the cartridge holder can be moved or both the receptacle holder and the cartridge holder can be moved relative to each other by the robotic component.

The analysis system can comprise a drive for driving the actors of the cartridges. When a required cartridge is in a dispensing position, the drive can be coupled to the actor for compressing the fluid chamber of that cartridge. A controller of the analysis system can control the robotic component and the drive such that a required mixture of reagents can be provided in the receptacle.

Some embodiments can be particularly advantageous as the overall cost for the analysis system can be minimized while the quality of the analysis can be optimized. This can be due to the fact that the quantities of the reagents that need to be dispensed for performance of an analysis can be minimized because of the microfluidic dispenser.

In particular, this can be due to the fact that no decay products of the reagents can be present on the microfluidic dispenser which may otherwise negatively influence the performance of the analysis of the biological sample. As such decay products can be essentially absent due to the design of the microfluidic dispenser, the quantities of the dispensed reagents can be minimized. Further, the concentration of the reagent may not be changed due to the evaporation of solvent from the fluid volumes remaining from former dispensing steps which can enable a higher degree of precision as to the amount and concentration of dispensed reagent.

A typical pipetting station can be replaced in the analysis system by a cartridge holder and a drive that can be implemented by a much simpler mechanical design which can require less maintenance and can be far less costly to produce. In particular, this can be due to the fact that the complex movement pattern that is executed by a pipetting station may be replaced by a translational motion of the cartridge holder relative to the receptacle holder.

Referring initially to FIG. 1, FIG. 1 shows a microfluidic dispenser 10. The microfluidic dispenser 10 can have a compressible elastomeric fluid conduit, such as, for example, a tube 12. The tube 12 can be formed by an elastomer, such as, for example, silicone rubber (VMQ, Methyl-Vinyl-Silicone-Rubber).

The tube 12 can have an upper end 14 and a lower end 16. A first check valve 18 can be mounted in the tube 12 above a second check valve 20. Hence, the check valves 18 and 20 can be distanced within the tube 12 in the direction 22 of the fluid flow. A fluid chamber 24 can be formed by the check valves 18, 20 and the portion of the tube 12 that can extend between the check valve 18 and the check valve 20.

The microfluidic dispenser 10 can be in a fluid connection with a fluid reservoir 26 that can contain a fluid 28, such as a reagent. The fluid reservoir 26 can have a connecting portion 30 for connecting the microfluidic dispenser 10 to the fluid reservoir 26.

For example, the check valve 18 may be fixed inside the tube 12 by a slip-fit. The check valve 18 may have a flange 32 that can have an outer diameter D that can be slightly larger than the inner diameter $d_T$ of the tube 12. Hence the check valve 18 can be slightly deformed in its mounting position fixing the check valve 18 to the interior surface of the tube 12 thus creating the slip-fit.

The check valve 20 may be attached to the tube 12 in the same way as the check valve 18. Alternatively and as shown in FIG. 1, the check valve 20 can have a flange 34 having an inner diameter d that can be slightly smaller than the outer diameter $D_T$ of the tube 12 such that a slip-fit can be created at the outer surface of the tube 20.

The check valve 20 can be a duckbill valve. The check valve 20 can be mounted on the lower end 16 of the tube 12. Its elastomeric lips 36 can extend beyond the lower end 16 of the tube 12 as depicted in FIG. 1.

The check valve 20 can be a passive unidirectional normally closed duckbill valve. The check valve 20 can comprise a cylindrical body member 52 provided with a fluid passageway 54. The body member 52 can smoothly taper from an inlet end 56 to form a wedge-shaped outlet end 58 having an outlet slit 59 defining the pair of resilient elastomeric sealing lips 36.

Figure 2:
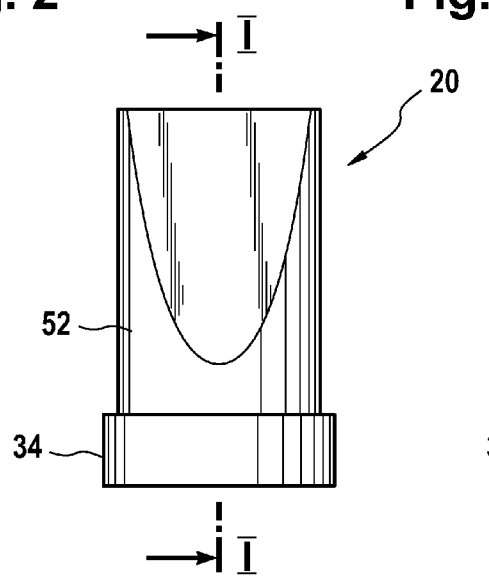
FIG. 2 illustrates a side view of a duckbill valve according to an embodiment of the present disclosure.
Figure 3:
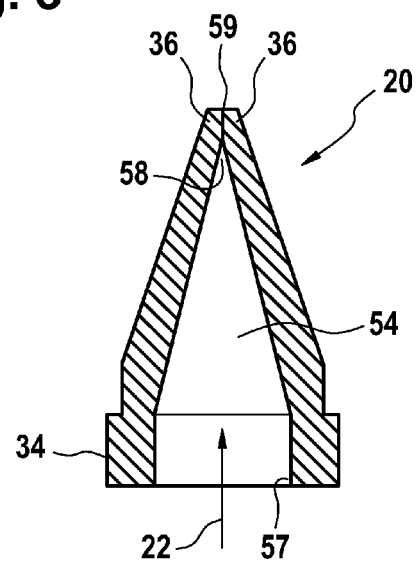
FIG. 3 illustrates a sectional view of the duckbill valve of FIG. 2 taken through plane I-I according to an embodiment of the present disclosure.
Figure 4:
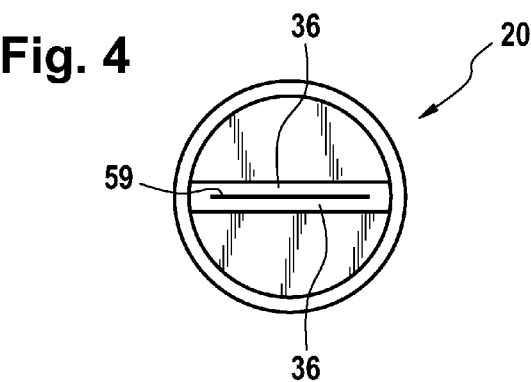
FIG. 4 illustrates a top view of the duckbill valve of FIG. 2 according to an embodiment of the present disclosure.

Body member 52 can be formed of a resilient elastomeric material which can be molded into the configuration shown in FIGS. 2 to 4. The check valve 20 can be sealingly positioned in line with the tube 12 as shown in FIG. 1. A flow of the fluid 28 can be directed along the tube 12 into the direction 22 along axial passage 54 to outlet end 58 where the pressure exerted by the fluid flow between the adjacent sealing lips can deform lips 36 away from one another to open outlet slit 59 of the check valve 20 to permit fluid flow therethrough.

If fluid flow stops or reverses direction, the resilient lips 36 can resume their normal shape into sealing arrangement against one another, closing the outlet slit 59.

The check valve 18 may be of similar or identical design as check valve 20, i.e. check valve 18 may also be a duckbill valve.

Actor 38 can be positioned in proximity to the fluid chamber 24. The actor may be a push rod that can be coupled to a drive (cf. drive 50 of FIG. 8 or 9) for controllably urging the actor 38 against the fluid chamber 24 such that the fluid chamber 24 can be compressed.

The lips 36 of the check valve 20 can form a sealing surface 82 that can also serve for evaporation protection of the fluid contained in the fluid chamber 24. The sealing surface 82 can form part of the outer surface of the dispenser 10 such that the fluid can be dispensed from the fluid chamber 24 through the check valve 20 directly into a receptacle, such as, for example, a sample tube 64 (cf. FIG. 13) without contacting any intermediary component of the dispenser 10. This can increase the precision with which the fluid can be dispensed and can also prevent the adhesion of fluid residuals on any intermediary component.

Figure 5:
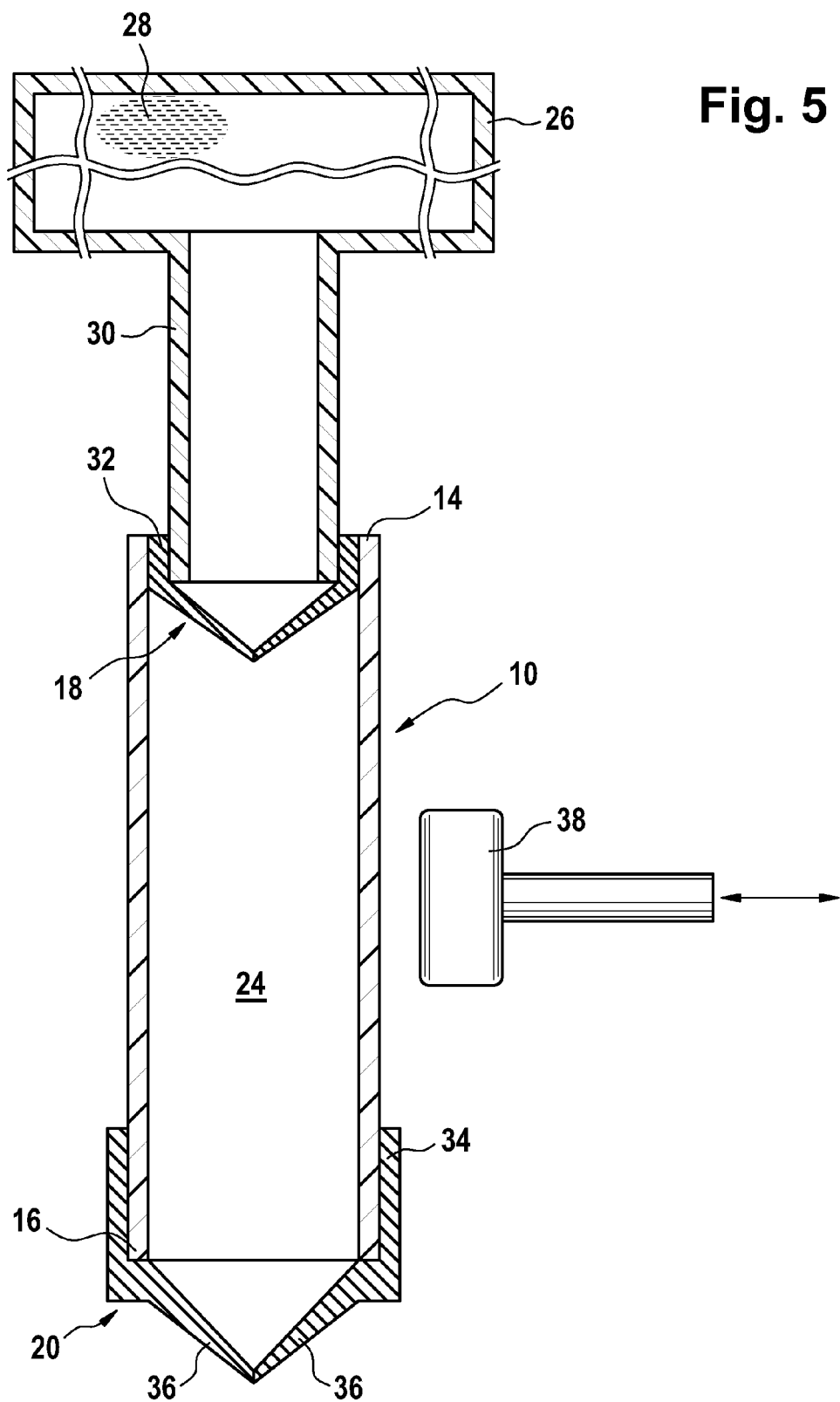
FIG. 5 illustrates a longitudinal cross-sectional view of the microfluidic dispenser according to another embodiment of the present disclosure.

FIG. 5 shows an alternative embodiment of the microfluidic dispenser 10. In this embodiment, the connecting portion 30 of the fluid reservoir 26 can form a slip-fit with the inner side of the flange 32 of check valve 18. For mounting the microfluidic dispenser 10 on the connecting portion 30, the following steps may be performed. Check valve 18 can be moved over the outlet opening formed by the connecting portion 30 to form a slip-fit between the inner side of the flange 32 and the outer side of the connecting portion 30; the upper end 14 of the tube 12 can be moved over the outside of flange 32 to form a slip-fit; and the check valve 20 can be moved over the lower end 16 of the tube 12 which can result in the arrangement as shown in FIG. 5.

Alternatively, the check valve 20 can be preassembled on the tube 12 such that the tube 12 with the already mounted check valve 18 can be moved over the flange 32 of check valve 18.

Alternatively, the microfluidic dispenser 10 can be integrally formed as a mold part such as by multi-component injection molding.

Figure 6:
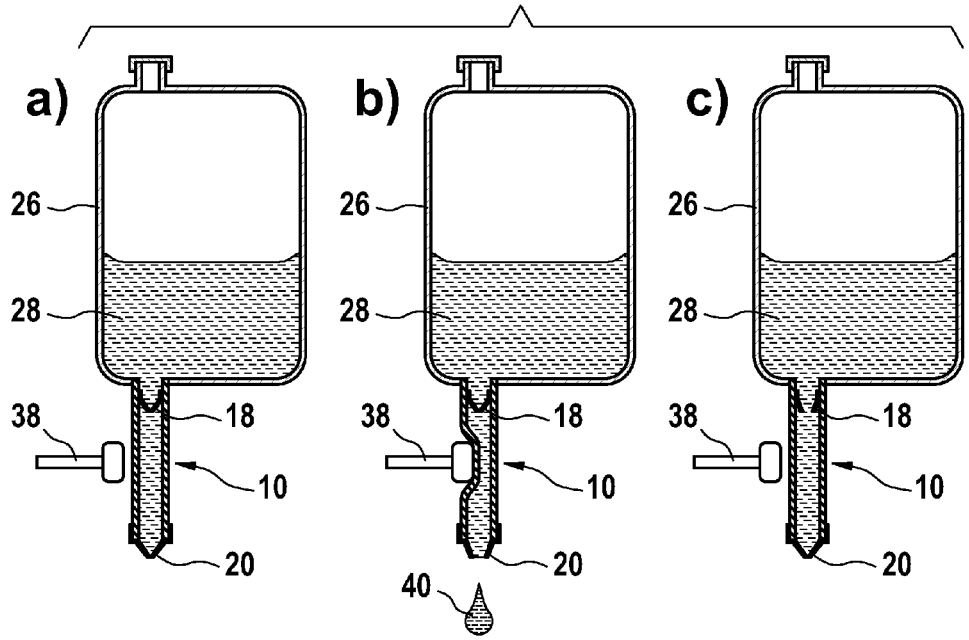
FIGS. 6a-c illustrate a first mode of operation of a microfluidic dispenser according to an embodiment of the present disclosure.

FIG. 6 illustrates a first mode of operation of the microfluidic dispenser 10. FIG. 6a shows the microfluidic dispenser 10 when the actor 38 is in its rest position. The fluid chamber 24 can be filled with a portion of the fluid 28. Both check valves 18 and 20 can be closed.

For dispensing a portion of the fluid 28, the actor 38 can be moved by the drive into the direction of the tube 12 such that the fluid chamber 24 of the tube 12 can be compressed as shown in FIG. 6b. The compression of the fluid chamber 24 can cause the check valve 20 to open such that the sealing lips 36 can be deformed for opening outlet slit 59. The opened sealing lips 36 can serve as nozzle for releasing a portion of the fluid 28, such as a droplet 40. As the sealing lips extend beyond the lower end 16 of the tube 12, there can be no risk that a portion of the droplet 40 can adhere to some portion of the microfluidic dispenser 10.

In one embodiment, the actor 38 can be displaced by a predefined distance such that only a relatively small portion of the fluid contained in the fluid chamber 24 can be dispensed.

Next, the actor 38 can be moved back to its rest position. This can cause the check valve 20 to close cutting off the fluid flow. The check valve 18 can be opened as the fluid pressure within the fluid chamber 24 is below the fluid pressure in the fluid reservoir 26 due to the fact that a portion of the fluid has been dispensed from the fluid chamber 22. As a consequence, the fluid chamber 24 can be refilled by a portion of the fluid 28 flowing from the fluid reservoir 26 into the fluid chamber 24.

For the embodiment of FIG. 6, a piezoelectric drive may be utilized for driving the actor 38 as the actor 38 may need to be displaced for a small predefined distance. If a larger volume of fluid needs to be dispensed, the sequence shown in FIGS. 6a-c may need to be carried out multiple times.

Figure 7:
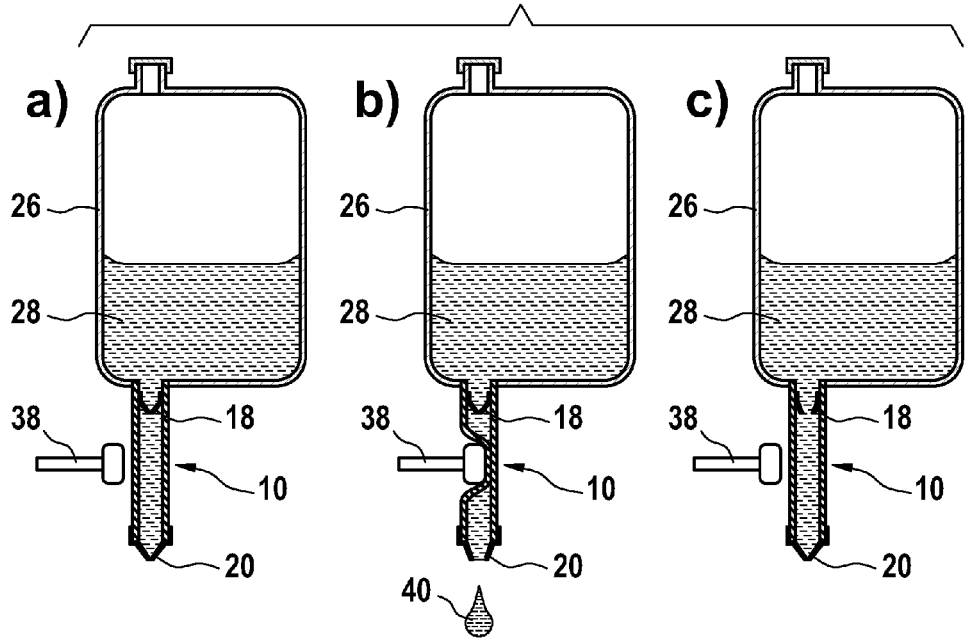
FIGS. 7a-c illustrate a second mode of operation of the microfluidic dispenser according to an embodiment of the present disclosure.

FIG. 7 illustrates a second mode of operation of the microfluidic dispenser 10. In this embodiment, a larger volume of fluid can be dispensed in one cycle due to a larger displacement of the actor 38. FIGS. 7a and 7c are equivalent to FIGS. 6a and 6c except that the amount of fluid flowing through the check valve 18 for refilling the fluid chamber 24 can be larger in FIG. 7c than it is in FIG. 6c.

As shown in FIG. 7b, the degree of compression of the fluid chamber 24 can be greater than that of FIG. 6b due to a larger displacement of the actor 38 resulting in a larger portion of the fluid 28 contained in the fluid chamber 24 being dispensed in one cycle. In this embodiment, a linear motor may be used for driving the actor 38 enabling a larger range of fluid volumes that may be dispensed by the fluid dispenser 10 in one cycle.

Figure 8:
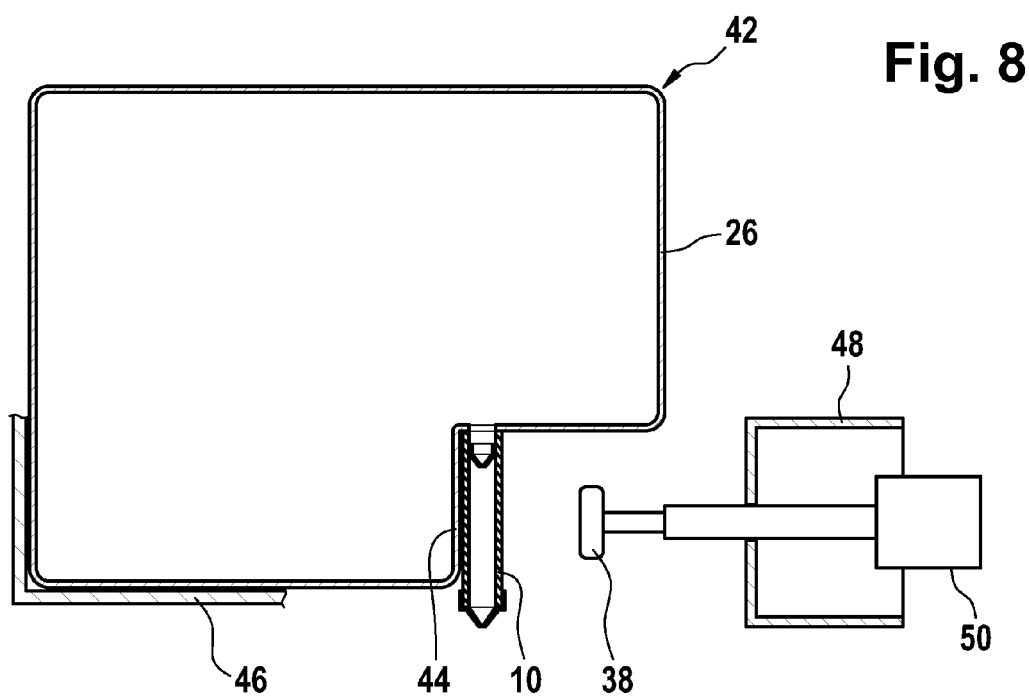
FIG. 8 illustrates a cartridge according to an embodiment of the present disclosure.

FIG. 8 shows an embodiment of a cartridge 42 that contains the reservoir 26 and the microfluidic dispenser 10. The cartridge 42 can have a wall portion 44. The fluid chamber 24 can extend along the wall portion 44 such that the wall portion 44 can form a counter-bearing when the actor 38 is urged against the fluid chamber 24 as shown in FIGS. 6b and 7b. The cartridge 42 can be inserted into a holder 46 of an analyzer 48. The analyzer 48 can have a drive 50, such as a piezoelectric drive or a linear motor for driving the actor 38.

Figure 9:
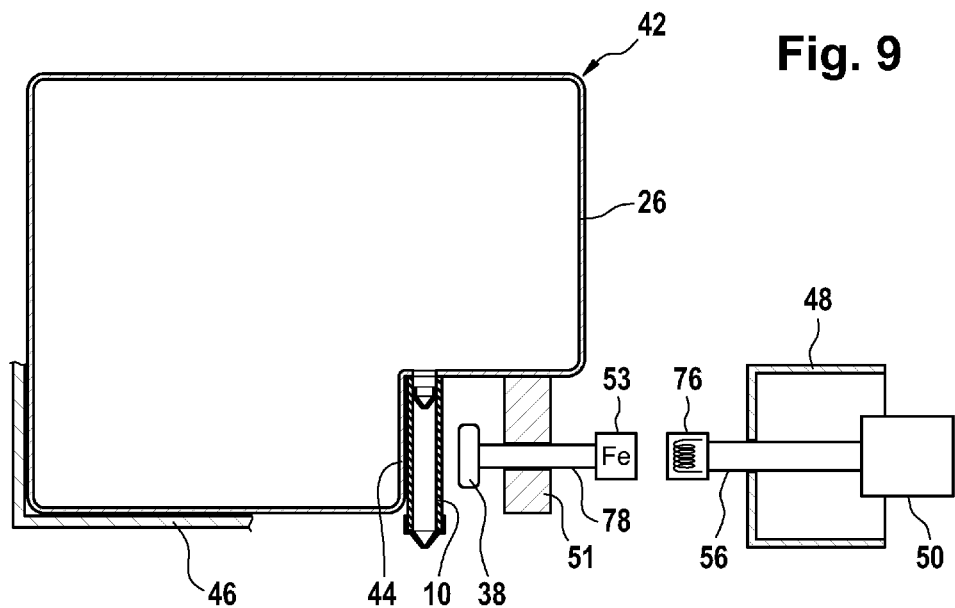
FIG. 9 illustrates an embodiment of a cartridge according to an embodiment of the present disclosure.

FIG. 9 shows an alternative embodiment where the actor 38 can form part of the cartridge 42. The cartridge can have a holder 51 for holding the actor 38 in its rest position in proximity to the fluid chamber 24. The actor 38 can be connected to a drive coupler 53 that can serve for coupling the actor 38 to drive 50. For example, the drive coupler 53 can be a ferromagnetic element.

The drive 50 can be connected to a rod 56. An electromagnet 76 can be mounted on the end of the rod 56. When the electromagnet 76 is excited by the analyzer 48, the ferromagnetic element of the drive coupler 53 can be attracted by the electromagnet 76 such that the actor 38 can be coupled to rod 56. The drive 50 may be controlled by the analyzer 48 to urge the actor 38 against the fluid reservoir 26 by a predefined distance or by a selectable distance depending on the implementation.

Figure 10:
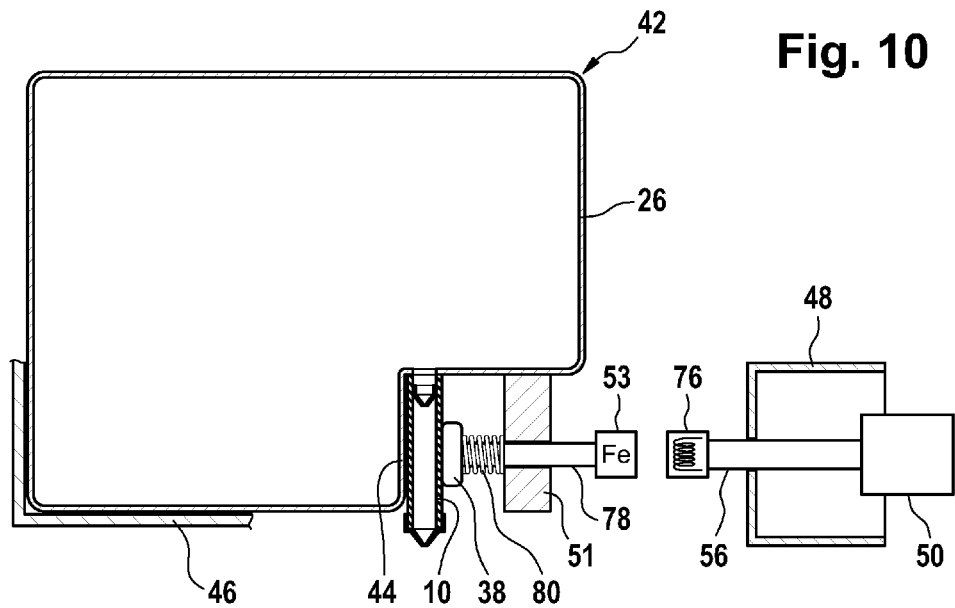
FIG. 10 illustrates another embodiment of a cartridge according to an embodiment of the present disclosure.

FIG. 10 shows another embodiment where the actor 38 can form part of the cartridge 42. As in the embodiment of FIG. 9, the holder 51 can hold a shaft 78 that can extend through the holder 51. The actor 38 can be formed on one end of the shaft 78 that is located opposite to the wall portion 44. The drive coupler 53 can be formed on the other end of the shaft 78.

A biasing element 80, such as a cylindrical spring as shown in FIG. 10, can exercise a biasing force onto the actor 38 towards the flow chamber 24 (cf. FIG. 1) in order to preposition the actor relative to the fluid chamber that is located between the wall portion 44 and the actor 38. For example, the biasing element 80 can extend between the actor 38 and the holder 51 in order to slightly press the actor 38 against the flow chamber 24 to keep the actor 38 in a defined position in close proximity to the flow chamber. This can be particularly advantageous if the drive 50 is a piezo-electric drive as a piezoelectric drive can move the shaft 78 only by very small increments.

In the embodiments shown in FIGS. 9 and 10, the rod 56 and the mounted electromagnet 76 can still be in a position away of the drive couple 53. In this configuration, the drive 50 can have to move the rod 56 and the mounted electromagnet 76 first into the direction to the drive couple 53 to bring the electromagnet 76 and the drive couple 53 into a smaller distance. Thereafter, the electromagnet 76 can be excited to attract the ferromagnetic element of the drive coupler 53 by the electromagnet 76 such that the actor 38 can be coupled to rod 56.

FIG. 11 shows an embodiment of a cartridge. In this embodiment, the holder 46 can be implemented as a docking station of the analyzer 48 for receiving three cartridges 42.1, 42.2 and 42.3. The cartridge 42.1 can comprise a fluid reservoir 26.1 and the microfluidic dispenser 10.1 in accordance with the embodiment of FIG. 9 thus including the actor 38.1. In contrast, the drive with the ferromagnetic element 76.1 can form part of the docking station and thus the analyzer 48. The other cartridges 42.2 and 42.3 can be of identical mechanical design but may contain other reagents. For example, each of the cartridges 42.1, 42.2 and 42.3 can contain one reagent of an immuno assay, such as, for example, an ECL (electrochemoluminescence) assay.

FIG. 11 shows the cartridge 42.1 before insertion into the holder 46 that can receive all three cartridges 42.1, 42.2 and 42.3. The cartridges 42.2 and 42.3 may have already been inserted into the holder 46.

Each of the cartridges 42.1, 42.2 and 42.3 can be a disposable whereas the docking station, i.e. the holder 46, can form part of the analyzer 48 that can also include the drive 50. In addition, the docking station may include a sensor 60 for each of the cartridges for sensing the amount of fluid dispensed from the respective microfluidic dispenser 10 and such that the analyzer 48 may correspondingly control the drive 50 for dispensing of a desired volume of the fluid 28 from the respective cartridge.

The cartridges 42.1, 42.2 and 42.3 may be implemented as separate physical components as shown in FIG. 11. Alternatively, these cartridges can be integrally formed such as by a single injection molded part that can unify the three cartridges of the immunoassay into a single physical component.

For clinical tests, typically, two different reagents may be required. In accordance with one embodiment, two of the cartridges, such as cartridges 42.1 and 42.2, can be integrally formed to form a single physical unit. The fluid reservoir 26.1 can contain one of the reagents whereas the fluid reservoir 26.2 can contain the other reagent that may be required for performing the clinical test.

FIG. 12 shows a top view of the holder 46 after the cartridges 42.1, 42.2 and 42.3 have been removed.

Figure 13:
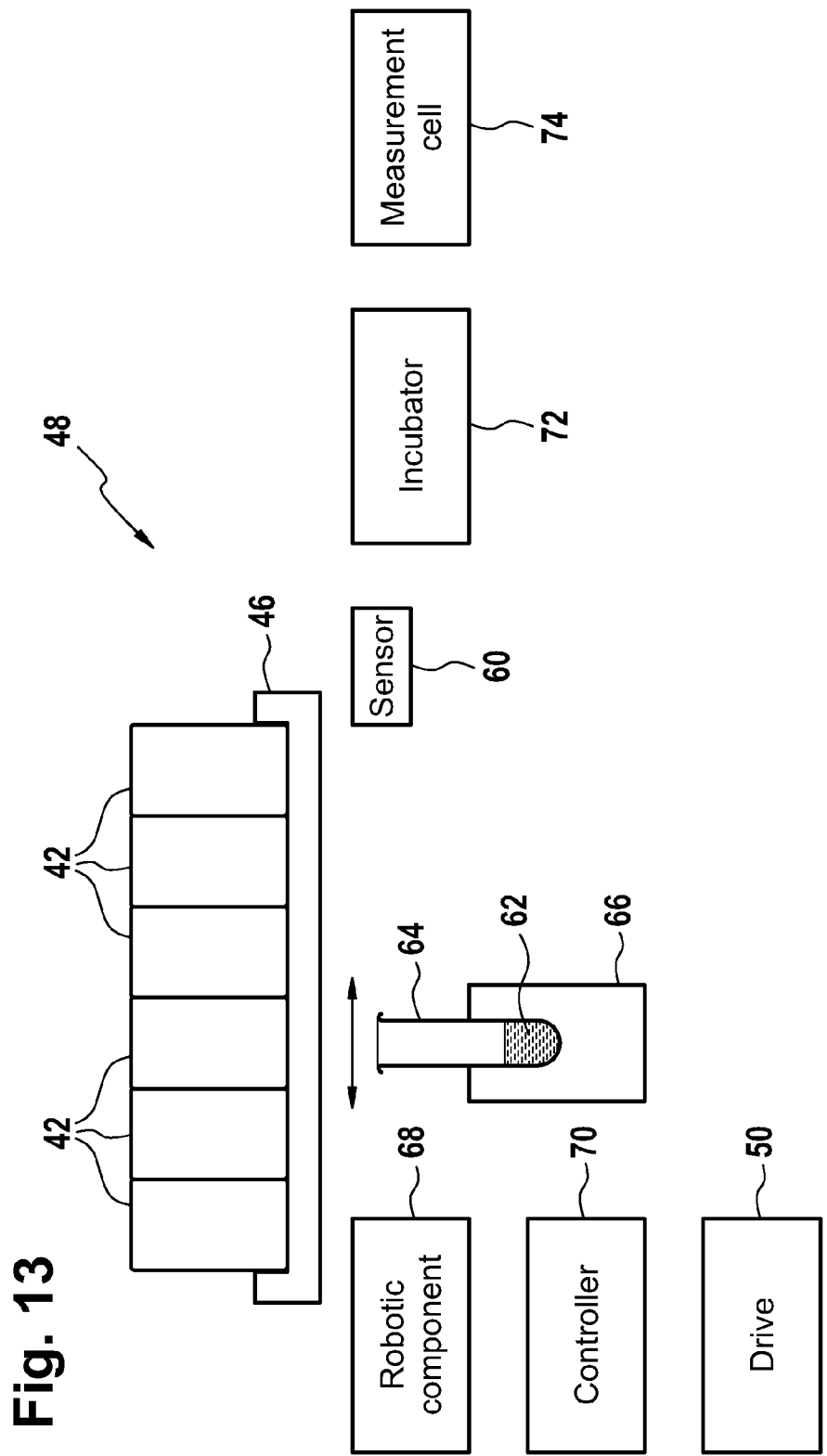
FIG. 13 illustrates an embodiment of an analysis system according to an embodiment of the present disclosure.

FIG. 13 shows a highly schematic block diagram of analyzer 48. Analyzer 48 can have a holder 46, such as a docking station (cf. FIG. 10) for receiving multiple disposable cartridges 42. Each one of the cartridges 42 may be filled with one of the reagents that can be required for analyzing a biological sample, such as, for example, a reagent of an immunoassay. Alternatively, at least one of the cartridges 42 can comprise multiple cartridges, such as cartridges 42.1, 42.2 and 43.3, that can be integrally formed as a single physical unit.

The biological sample 62 to be analyzed can be contained in a sample tube 64 that can be held by a tube gripper 66 of the analyzer 48.

The analyzer 48 can have a robotic component 68 for a relative movement of the holder 46 and thus the cartridges 42 and the tube gripper 66 for positioning the sample tube 64 underneath one of the cartridges 42 from which a portion of a reagent may need to be dispensed into the sample tube 64. The analyzer 48 can have a controller 70 for controlling overall system operation, such as a computer. Further, the analyzer 48 may comprise an incubator 72, and a measurement cell 74 as well as other components depending on the type of the analysis to be performed.

In operation, the controller 70 can control the robotic component to position the tube gripper 66 with the sample tube 64 underneath one of the dispensers of one of the cartridges 42 that can contain a reagent that may need to be dispensed into the sample tube 64. When the sample tube 64 has been positioned under the required dispenser, the controller 70 can control the drive 50 to push the actor 38 against the fluid chamber 24 of that dispenser such that a portion of the reagent can be dispensed. This may be repeated several times until the required mixture of reagents is present in the sample tube 64.

Next, the sample tube 64 may be moved to the incubator 72 for incubation of the mixture. After incubation, the controller 70 can control the measurement cell 74 to perform a measurement for analyzing at least one property of the sample 62. The controller 70 can output this result via a machine or user interface.

Figure 14:
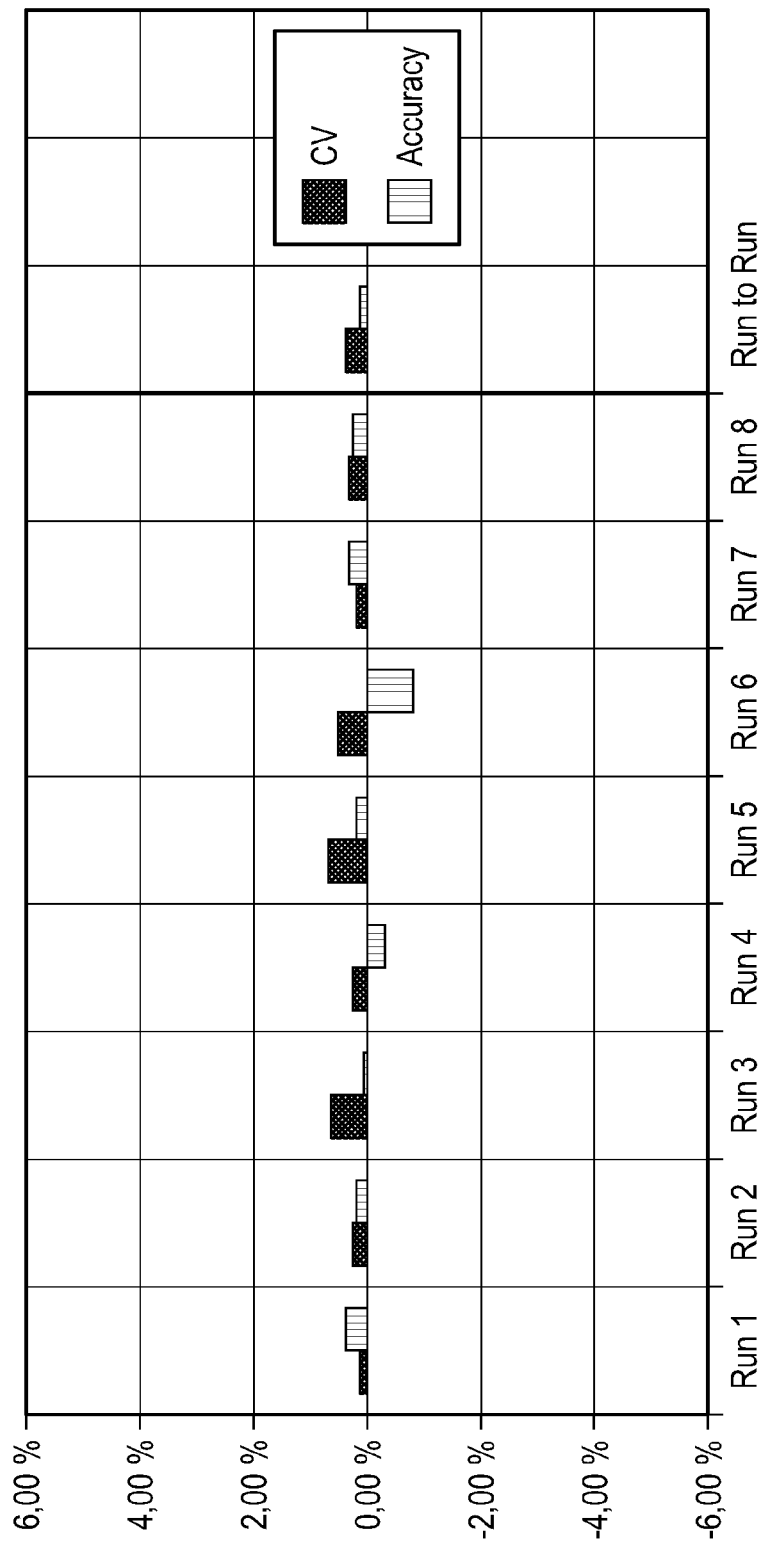
FIG. 14 illustrates the precision of an embodiment of a dispenser of the invention when water is dispensed according to an embodiment of the present disclosure.
Figure 15:
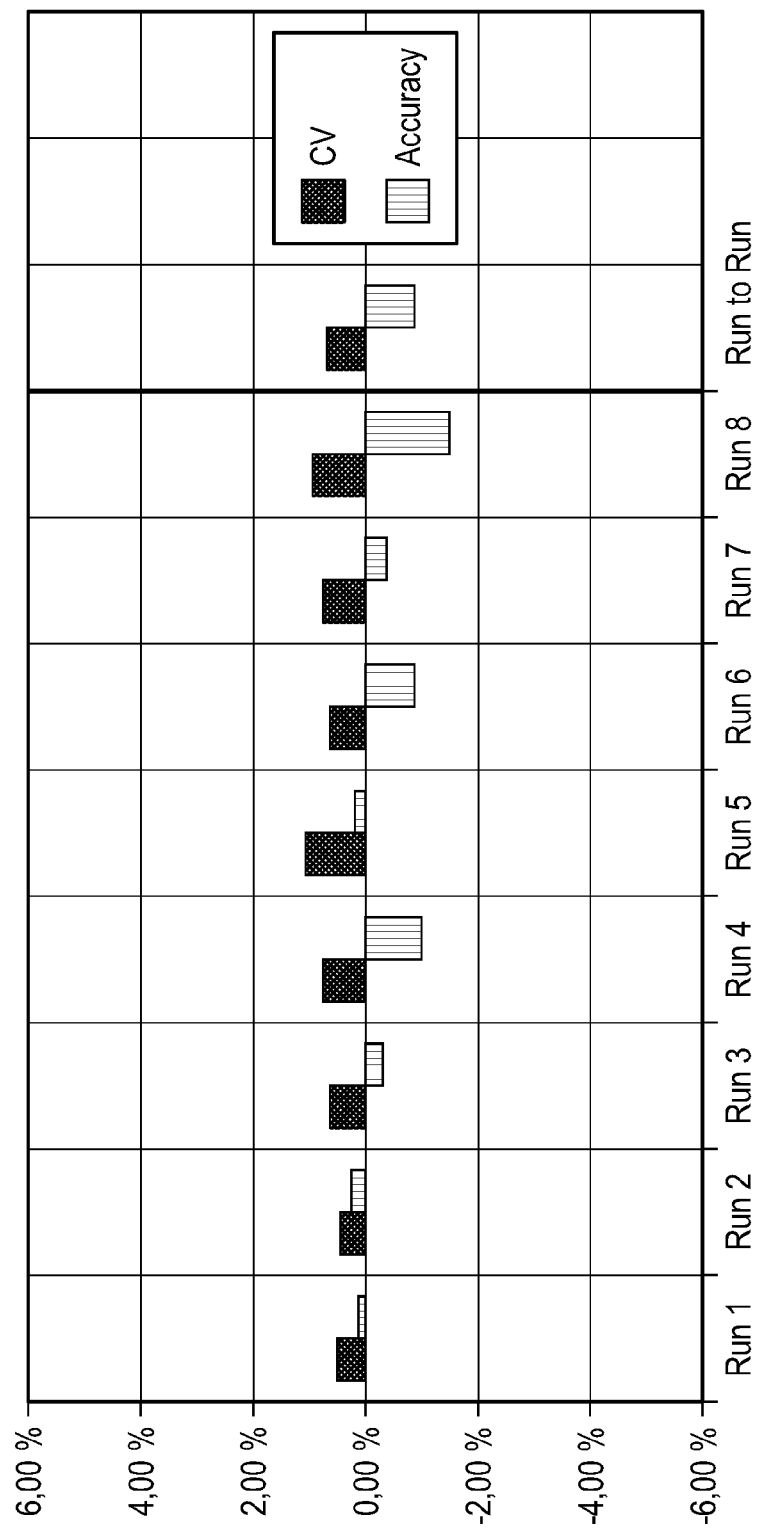
FIG. 15 illustrates the precision of an embodiment of a dispenser of the invention when another fluid is dispensed according to an embodiment of the present disclosure.

FIGS. 14 and 15 are diagrams illustrating the precision with which various types of fluids can be dispensed using an embodiment of the microfluidic dispenser. FIG. 14 illustrates experimental results obtained by dispensing water. The viscosity of water is about 1.0 mPas at 20° C. and about 0.8 mPas at 25° C. The target volume of water to be dispensed in each one of the dispensing steps is about 1 µl. A run of dispensing steps can comprise twenty-seven subsequent dispensing steps each with a target volume of about 1 µl. Eight runs of twenty-seven dispensing steps of about 1 µl each has been performed as Run 1 to Run 8. FIG. 14 shows the CV (coefficient of variation) and the accuracy for each of the runs and also run to run.

FIG. 15 shows the same diagram for another fluid having a higher viscosity of about 17 mPas for which a similar precision is obtained.

FIG. 16a shows an embodiment of the microfluidic dispenser 10 wherein the check valve 20 can be rotationally symmetric around the longitudinal axis 86 that can extend along the tube 12. The symmetrical check valve 20 can be formed of an elastic material that can have an elastic pre-tension to keep the circular outlet 84 of the check valve 20 normally-closed as shown in FIGS. 16a and 16b. The valve body of the second check valve 20 can constitute a sealing surface 82 that can form part of the outer surface of the dispenser 10 such that the fluid can be dispensed directly from the second check valve into a receptacle, such as a sample tube 64 (cf. FIG. 13) without any intermediary components.

FIGS. 17a and 17b show the dispenser 10 in its open state when the actor 38 (cf. FIG. 1, 5, 6, 7, 8, 9, 10, 11) can exercise a mechanical force onto the tube 12 such that the tube can be compressed and the symmetrical check valve 20 can be opened due to the increased fluid pressure. Due to the opening pressure, the circular outlet 84 can be opened by elastic deformation of the symmetrical valve body against its elastic pre-tension.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A cartridge for dispending a fluid, the cartridge comprising:
    a reservoir for the fluid;
    a dispenser for dispensing the fluid, wherein the dispenser comprises a compressible elastomeric fluid conduit having a first end and a second end for flowing the fluid from the first end to the second end, a first check valve and a second check valve distanced in the conduit for forming a fluid chamber, wherein at least the second check valve is a duckbill valve or a rotationally symmetrical valve having a circular fluid outlet, wherein the second check valve is located at the second end of the conduit, wherein the second check valve has sealing lips that extend beyond the second end of the conduit, and wherein the dispenser has its first end connected to the reservoir for enabling an inflow of the fluid from the reservoir into the fluid chamber through the first check valve;
    a wall portion, wherein the fluid chamber extends along the wall portion; and
    an actor for compressing the fluid chamber for dispensing a portion of the fluid, wherein the actor presses the fluid chamber against the wall portion for compressing the fluid chamber.

2. The cartridge of claim 1, further comprises,
    a biasing element for exercising a biasing force onto the actor in order to preposition the actor relative to the fluid chamber.

3. The cartridge according to claim 1, further comprises,
    a holder for holding the actor in proximity to the fluid chamber and for guiding the actor towards the fluid chamber when the actor is urged against the fluid chamber by a drive.

4. The cartridge according to claim 3, wherein the actor has a drive coupler for releasably coupling the actor to the drive.

5. The cartridge according to claim 4, wherein the drive coupler has a ferromagnetic element for releasably coupling the actor to the drive.

6. The cartridge according to claim 5, wherein the ferromagnetic element is a jawed chuck, a vacuum chuck or a collet.

7. The cartridge according to claim 1, wherein the fluid contains a reagent.

8. An analysis system for analyzing a biological sample, the analysis system comprising:
    a cartridge holder for holding a plurality of the cartridges according to claim 1;
    a receptacle holder for holding a receptacle containing the biological sample;
    a robotic component for relative movement of the cartridge holder and the receptacle;
    a drive for driving actors of the cartridges; and
    a controller for controlling the robotic component and the drive for dispensing one or more reagents from the cartridges into the receptacle for inducing a reaction of the biological sample with the one or more reagents to perform the analysis.

9. The analysis system according to claim 8, further comprising,
    a sensor for sensing the volume of a fluid dispensed from one of the cartridges and for generating a sensor signal indicative of the volume, wherein the controller receives the sensor signal and controls the drive for dispensing a predetermined volume of the reagent from one of the plurality of cartridges.

* * * * *